United States Patent [19]
Lee et al.

[11] Patent Number: 6,156,272
[45] Date of Patent: Dec. 5, 2000

[54] METHOD AND APPARATUS FOR URINE SELF-TEST INTENDED FOR USE IN A TOILET

[75] Inventors: Steven H. Lee; Barry F. Lillard, both of Conway, Ak.

[73] Assignee: All Technologies Corporation, Vero Beach, Fla.

[21] Appl. No.: 09/098,260

[22] Filed: Jun. 16, 1998

Related U.S. Application Data

[63] Continuation-in-part of application No. 08/870,674, Jun. 6, 1997, abandoned.

[51] Int. Cl.[7] .......................... G01N 21/00; G01N 21/01; G01N 33/72; G01N 21/77; C12Q 1/70
[52] U.S. Cl. .................. 422/58; 422/55; 422/56; 422/57; 422/58; 422/59; 422/60; 422/61; 436/66; 436/169; 436/177; 436/178; 436/808; 436/810; 436/816; 435/5
[58] Field of Search .............................. 436/66, 169, 177, 436/178, 808, 810, 814; 422/55–61; 435/5

[56] References Cited

U.S. PATENT DOCUMENTS

| | | |
|---|---|---|
| 4,725,553 | 2/1988 | Guadagno . |
| 5,356,782 | 10/1994 | Moorman et al. . |
| 5,536,564 | 7/1996 | Noda . |
| 5,786,220 | 7/1998 | Pronovost et al. . |
| 5,877,028 | 3/1999 | Chandler et al. . |

*Primary Examiner*—Nita Minnifield
*Assistant Examiner*—Padma Baskar
*Attorney, Agent, or Firm*—Lathrop & Gage, L.C.; Joseph L. Johnson; William A. Rudy

[57] ABSTRACT

A method and apparatus for urine self testing wherein the apparatus is placed directly into the toilet after urination which avoids the direct placement and retention of an apparatus in the stream of urine as is common with urine testing devices. The apparatus detects the presence of certain chemicals in dilute urine such as the presence of human chorionic gonadotropin (hCG) in the urine of a pregnant woman. An opening in the apparatus is fitted with a fluid absorption device which acts to concentrate the diluted urine on an indicator strip which contains antibodies, enzymes and antibody blockers which will provide a reactive change, usually of color, when subjected to a predetermined chemical such as hCG. The apparatus functions in dilute urine when placed in a toilet after urination and is largely constructed of biodegradable materials so that it can be flushed into the sewage system or a septic tank. The apparatus may be fitted with an optional tether so that the apparatus may be removed from the toilet after use if flushing the apparatus is not desirable.

11 Claims, 2 Drawing Sheets

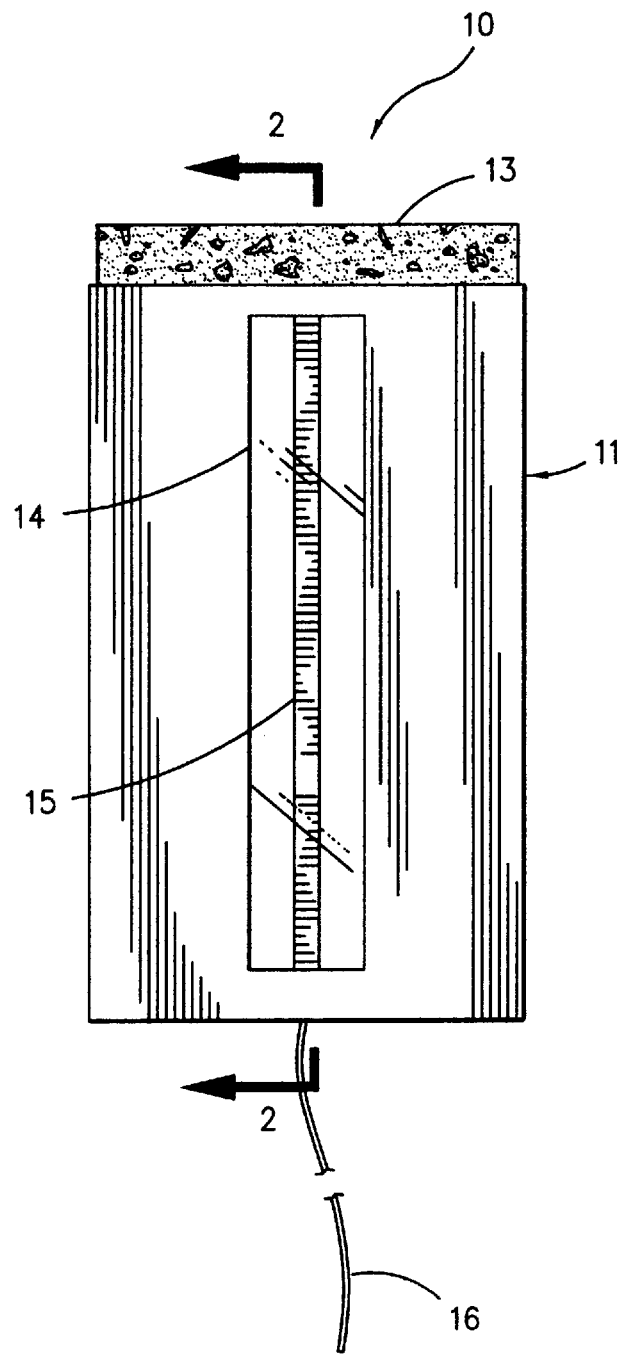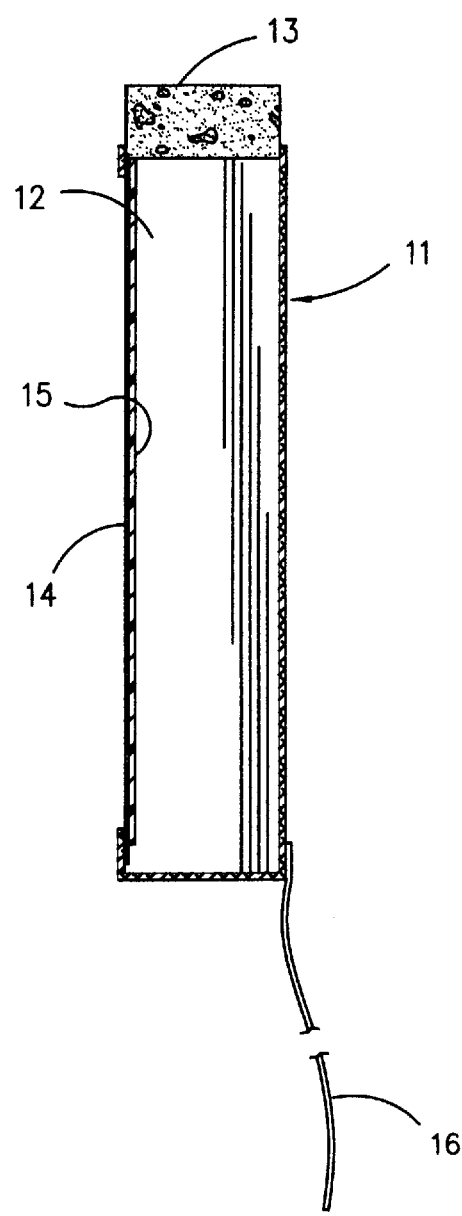

METHOD AND APPARATUS FOR URINE SELF-TEST INTENDED FOR USE IN A TOILET

This is a Continuation-in-Part Application, pursuant to 37 C.F.R. §1.53(b), from U.S. application Ser. No. 08/870,674 filed Jun. 6, 1997 now abandoned.

BACKGROUND OF THE INVENTION

1. Field of the Invention

The present invention relates to an improved method and device for determining the presence of certain components in human urine. In particular, the present invention is directed to a urine self-test device, comprised of biodegradable materials, which can be placed directly into the toilet after urination for detection of predetermined substances which may be found within the urine. While the invention can be configured to detect any substance ascertainable within urine, the invention is directed particularly to urine testing for pregnancy.

2. Description of the Related Art

Many medical diagnostic tests require the detection of specific components which are found in urine specimens. Most medical tests for the presence of components in the urine are conducted in a laboratory. However, there are many benefits to self-administered medical tests including decreased costs, saving of time and increased privacy. The most common example is that of the home pregnancy test which generally utilizes a human chorionic gonadotropin (hCG) indicator which changes color if hCG is found in the urine which is suggestive of pregnancy.

Despite the advantages of self-testing, the handling of urine and urine-ladened test devices is objectionable. Further, the disposal of non-biodegradable testing devices can be objectionable, particularly when privacy is desired and the device can not be conveniently or discretely disposed.

At present, devices are available for self-administered urine testing for: pregnancy, pathological growths such as hydatiform mole or choriocarcinoma which may cause hCG secretion and for determining blood in the urine. There is an increase in self-administered medical testing specific to urine due to the ease of testing, decreased medical cost and generally decreased time for return of test results. While there has been an overall increase in self testing, pregnancy testing in particular has greatly improved over the past few decades. Early pregnancy tests required a visit to a physician who would draw blood and conduct fairly elaborate chemical tests, often requiring the use of a host animal which had to be killed. Further, it could take several days for the return of the test results. Laboratory methods eventually developed which avoided blood sampling, and the death of animals, by conforming the test process to urine samples in which can be detected hCG during pregnancy. A home sampling test was developed as disclosed in U.S. Pat. No. 4,315,908, although the sample had to be sent to a laboratory for analysis by radioimmunoassay. Finally, a test was developed which allowed a home pregnancy test to be totally self-administered with results available in just a few minutes.

Several companies manufacture home pregnancy tests which are available on the market at nominal prices. All of the home pregnancy tests currently available utilize a specimen collector or indicator which is held in the stream of urine during normal urination or dipped into a container of collected urine. If the woman is pregnant, it is likely that hCG will be secreted within the urine. A predetermined indicator such as a monoclonal antibody specific to the beta subunit of hCG is provided by the testing device and will change color, or provide some other visible indication, if hCG is present and detected. It is well known within the art how to provide reagents which change color, or provide some visible reaction, when subjected to urine containing hCG, even in dilute amounts which may be present in a toilet bowl after urination. Most of the available testing devices also provide a control indicator to show that the test performed as indicated. However, the indicator portion of the test device is often small with the color differentials between a positive result and a negative result being difficult to distinguish. Some of the test devices provide a + or − symbol for positive or negative results, with the symbols being so small as to require close and careful inspection of the urine laden device.

The known home pregnancy tests have several other problems. Women are generally dissatisfied with the present devices due to the necessity of holding the test indicator directly in the stream of urine, or collecting urine in a specimen container so that the indicator may be placed therein. Either of these methods often produce the undesirable result of contacting the urine stream with a hand or clothing. Further, during the requisite period of waiting for the test results, the device must either be held in the hand or placed on a level surface which increases the likelihood of dripping or spilling urine. After the test is completed, the indicator device must be disposed into the trash, often resulting in the further dripping or spilling of urine. While some of the testing devices function properly in diluted urine, they are not suitable for disposal into the sewer system for physical reasons of structural stability, size and inert or non-biodegradable content. Further, the small indicator portions provided on the known test devices can not be seen without close inspection.

Pregnancy test results can produce a wide range of emotion and the experience is not enhanced by the perceived nastiness of the testing process. Additionally, if the testing process is a private matter, the secrecy of the process may be jeopardized if the test indicator is not properly disposed. It is desirable to have a test indicator which does not have to be handled after it is subjected to contact with urine and which does not have to be disposed of in the trash.

It is an object and purpose of this invention to provide an urine test device which does not have to be handled after being subjected to urine.

It is also an object and purpose of this invention to provide a visibly reactive response to the presence of hCG in dilute urine, with the reactive response readily visible to the user.

It is a further object and purpose of this invention to allow the user of the urine test device to read the results from a distance, particularly while it is in the toilet bowl containing dilute urine.

Yet another object and purpose of this invention is to provide a biodegradable alternative to the known urine test devices thereby allowing the urine test device to be safely flushed into a sewage system or septic system.

SUMMARY OF THE INVENTION

The home testing device of the present invention provides a method and apparatus that overcomes the stated deficiencies of the prior art as it allows the user to place the device directly into the toilet after urination where the test results can easily be viewed and as it is flushable into the sewer system by the nature of being compact and biodegradable. The device may be placed into the toilet after urination by dropping or by suspending it on a tether. The device will float in the toilet and will provide either a positive or false indication after a predetermined duration of exposure to the dilute urine.

The device can be constructed with indicator viewing areas on both planar surfaces so that the device can be dropped into the toilet in any position. Alternatively, if only one indicator viewing port is provided a tether can be affixed to the device so that the view port remains oriented upward when the device is lowered into the toilet. The indicator viewing areas will be of sufficient size so that the test results can be easily viewed at a reasonable distance.

All of the device which has come into contact with urine will be biodegradable and may be flushed into a sewage system or septic system leaving only a sanitary wrapper to be disposed. Alternatively, in a situation where solids are not desired to be introduced to the sewage system, the optional tether may be used to suspend the device in the toilet during the test and then to retrieve the device for disposal without necessitating direct contact with the contaminated portion of the device.

Variables inherent in most medical testing, as with urine specific pregnancy testing, are well known within the art. It is also known by those skilled in the art of home pregnancy testing the parameters necessary to obtain accurate test results of positive gonadotropin presence indicative of pregnancy. Dilute volumes of urine may be accurately tested using indicator devices currently available on the market, such as the pregnancy indicator device marketed under the trade name Early Pregnancy Test (E.P.T.) or the QuickVue device manufactured by Quidel Corporation. Further, testing discloses that pregnancy indicator devices readily available on the market, such as those indicated above, perform accurately when subjected to common household cleaners and disinfectants used in toilet bowls.

Inherent in home testing devices is the statistical likelihood of a false result due to variables not normally present in clinical testing environments. Manufacturers can not develop home testing devices which overcome any and all variables and typically solve this problem by providing instructions and directions with the testing device to eliminate or control variables and to warn the user of possible false results when the testing is not conducted in a controlled environment. Most existing devices direct users to test urine after sleeping because urine volume will be great as will the urine concentration. For the instant device, it is necessary to provide instruction and direction to the ultimate user such as is currently provided with the earlier types of home pregnancy devices.

While experimentation shows that devices currently available on the market will accurately perform in most environments normally found in residential toilets, cautionary information will necessarily be provided to the consumer. Experiments were conducted using pregnancy indicator devices commonly used and well known within the industry. Variables were utilized to closely simulate conditions common to residential toilets. Toilets having varying water levels between six (6) and eight (8) liters were tested using between fifty (50 mL) and one hundred milliliters (100 mL) of urine. Further, experiments were conducted where common toilet bowl cleaners were incorporated into the varying levels of water within a toilet bowl. All experiments using the subject invention, wherein the test indicator strip was comprised of hCG detection components readily found in over the counter pregnancy testing devices, provided highly accurate and consistent readings. Between fifty (50 mL) and one hundred (100 mL) milliliters of urine from a pregnant female, less than the average urination volume, will provide a positive reaction for the presence of hCG when diluted in approximately six to eight liters of water, the amount found in most residential toilets, using known visual indicators similar to those currently available.

It is necessary to ensure direct contact of urine, even in dilute amounts, with the indicator device. Therefore, in one configuration of the invention, a wicking device is secured to one end of a housing, which encompasses the indicator strip, which facilitates the movement of dilute urine into the housing for direct contact with the indicator strp. Another configuration of the invention uses a planar housing which lies flat on, or near, the surface of the liquid within the toilet bowl, thereby allowing the indicator device to directly contact the dilute urine.

Yet another configuration of the invention provides the paper-like indicator device encircled about a cylindrical wick. The wick absorbs the dilute urine through the open ends and disposes the dilute urine directly onto the indicator device. The entire surface of the indicator will be provided with reagent which changes color in the presence of predetermined substances within urine, such as hCG. The device will have a clear protective covering over the indicator to maintain its integrity during the testing process.

In any of the configurations described, each component will be constructed of biodegradable materials which do not immediately decompose or alter configuration when subjected to the test liquid for a period of time sufficient to allow the reagents provided on the indicator to react to components within the urine, if any. The invention, in any of the described configurations, will be provided with a negative control on the indicator device which will visibly change color after the invention has been subjected to the dilute urine for a period of time sufficient to produce a positive reaction in the presence of the predetermined component within urine, thereby signaling the user that the device worked correctly, but the sought analyte was simply not present. In the case of pregnancy testing, when the negative control changes color, but the indicator device does not, it will signal the user that no hCG is present and that pregnancy is not likely indicated.

As is known within the art, visible reaction to the presence of hCG may be accomplished by using an indicator provided with an antibody and enzyme reactive to a component of hCG. Even very dilute amounts of urine from a pregnant woman contains sufficient amounts of hCG for components found within hCG to attach to the antibody provided and to initiate a color change within the antibody indicative of molecular binding between the antibody and components of the hCG, thereby indicating the presence of hCG within the urine.

BRIEF DESCRIPTION OF THF DRAWINGS

FIG. 1 is a front view of a biodegradable urine self test device constructed in accordance with the present invention.

FIG. 2 is a sectional view from the side of a biodegradable urine self test device constructed in accordance with the present invention.

DESCRIPTION OF THE PREFERRED EMBODIMENTS

Figures 3, 4:
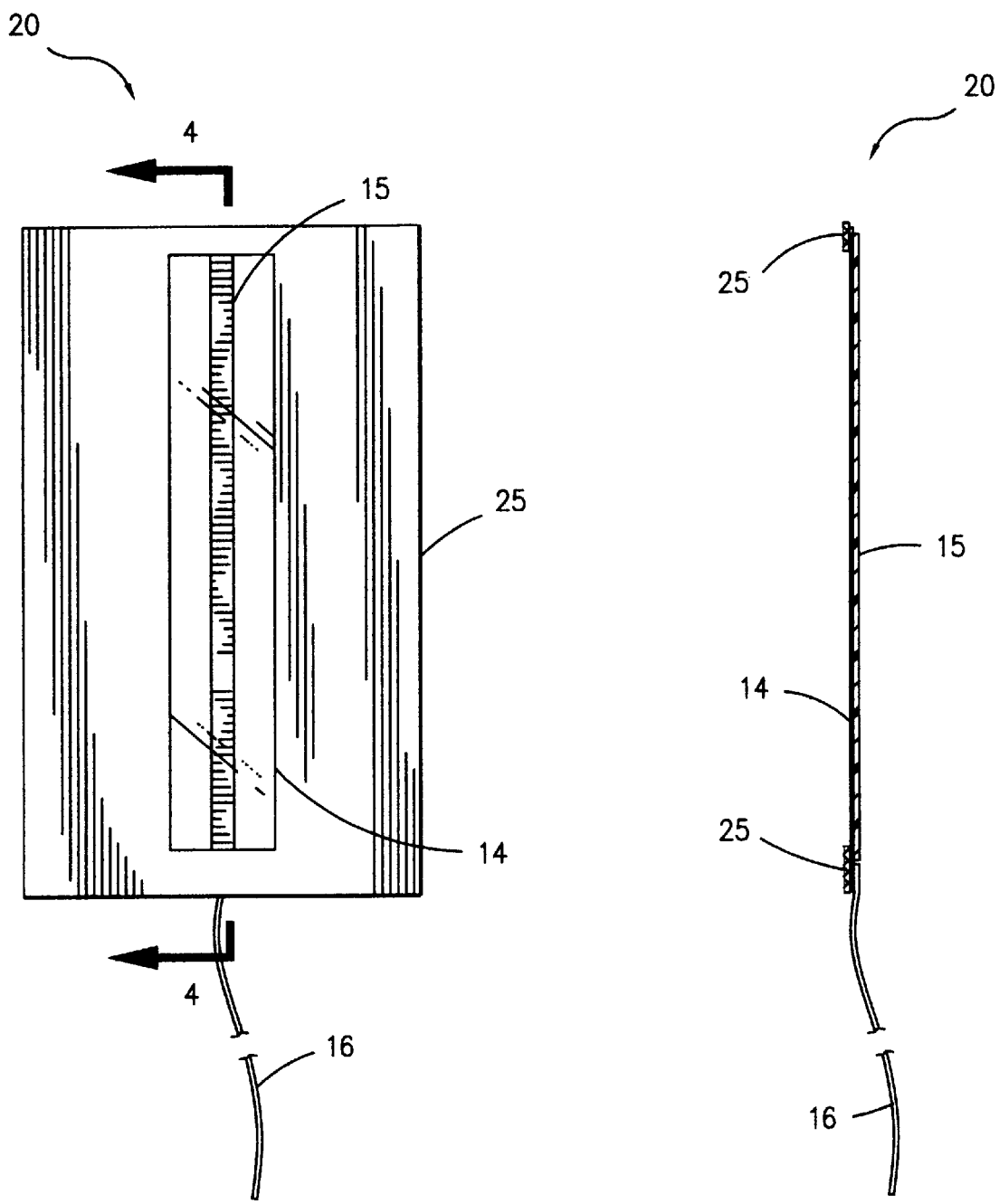
FIG. 3 is a front view of another version of the present invention which is a planar biodegradable urine self test device for direct contact with dilute urine.
FIG. 4 is a side view of another version of the present invention which is a planar biodegradable urine self test device for direct contact with dilute urine.

Referring to the drawings in detail, FIG. 1 illustrates an overall view of a biodegradable urine self test device 10 constructed in accordance with the present invention.

The biodegradable urine self test device 10 includes a housing 11 which is generally box shaped and having a fluid collection chamber 12 therein. In the present embodiment, the housing 11 is constructed of buoyant biodegradable material which will be stable in liquid for a predetermined period of time sufficient for the completion of testing and which will then begin to break apart. At one end of the housing 11 is a fluid absorption means 13 which facilitates the passage of fluid into the chamber 12. A view site 14 is provided on at least one planar face of the housing 11 which allows visual access to a test indicator strip 15 which is affixed to the housing 11 such that it is in fluid communication with the chamber 12 when the biodegradable urine self test device 10 is subjected to liquid, particularly water and urine within a toilet.

The test indicator strip 15 is provided with an enzyme, an antibody and an antibody block as is known within the art and which causes a reactive change in color when coming into contact with human chorionic gonadotropin (HCG) which is found in the urine of pregnant women.

A tether 16 is fixed to the housing 11 such that the device can be retrieved from the toilet in the event it is undesirable to introduce the device into the sewage or septic system. In the event that the device is provided with only one view site 14 and test indicator strip 15, the tether 16 may be used to ensure that the device floats with the view site 14 up.

Referring to FIG. 2, a sectional view from the side of the preferred embodiment is shown. The fluid absorption means 13 is shown in fluid connection with the chamber 12 and is fixed to the housing 11 a predetermined distance from the test indicator strip 15. Liquid is drawn through the fluid absorption means 13 and into the chamber 12 where it comes into contact with the test indicator strip 15. Once the chemical components within the urine cause a change in the chemical structure of the test indicator strip 15, a color change will occur to visually indicate positive or negative presence of a predetermined component. The resulting color change will be viewed through the view site 14.

FIG. 3 shows another embodiment of the inventive planar biodegradable urine self test device 20 which comprises a substantially planar housing 25, a view site 14 passing therethrough and a test indicator strip 15. Placement of the self test device 20 into a toilet bowl after urination brings the test indicator strip 15 into direct contact with the liquid in the toilet bowl. The test indicator strip 15 is provided with chemicals of predetermined combination which will provide a visible color change when subjected to certain chemicals which may be found in human urine. The view site 14 provides a visual point for detecting color changes on the test indicator strip 15 which results from changes in the chemical structure of the indicator strip when coming into contact with liquid, depending on the components of the liquid. The view site 14 allows visual inspection of the test indicator strip 15 from either side of the planar housing 25. A tether 16 is fixed to the planar housing 25 such that the device can be retrieved from the toilet in the event it is undesirable to introduce the device into the sewage system or septic system.

FIG. 4 is a side view of the planar biodegradable urine self test device 20 showing the positioning of the tether 16.

The cylindrical device is placed into the toilet after urination, where dilute urine is absorbed through opposing ends 36 of the cylindrical wick 32 and is disposed onto the indicator strip 32 which may react according to its composition and the presence of a specific analyte which may naturally occur in urine. The device may further be provided with a protective sheath 38 encircling the indicator strip 32 to maintain the integrity of the indicator strip 32 during the test period. All components of the inventive device are biodegradable and may be incorporated into a sewer or septic system.

Whereas the present invention has been described in relation to the drawings attached hereto, it should be understood that other and further modifications, apart from those shown or suggested herein, may be made within the spirit and scope of this invention.

What is claimed is:

1. A urine test apparatus for use in dilute urine which comprises:
    (a) a biodegradable housing constructed of materials which can be incorporated into a sewer system, further having a chamber therein, said biodegradable housing further having at least one opening therein, and wherein, upon placement of said biodegradable housing in liquid, the chamber is in fluid communication with the liquid;
    (b) at least one view site in a predetermined orientation in said biodegradable housing;
    c) at least one test indicator strip fixed in a predetermined orientation within said chamber wherein the at least one indicator strip can be viewed through said at least one view site, said at least one test indicator strip further comprising a predetermined chemical composition which provides a visible reaction to at least one chemical which may be found in human urine; and
    (d) a tether attached to the biodegradable housing and structured to allow the urine test apparatus to be lowered into and retrieved from a toilet.

2. A urine test apparatus as set forth in claim 1 further comprising a fluid absorption device attached to the biodegradable housing and which covers said at least one opening provided in said biodegradable housing wherein, upon placement of the biodegradable housing in liquid, the fluid absorption device facilitates the flow of liquid into the chamber of said biodegradable housing.

3. A urine test apparatus as set forth in claim 1 wherein said at least one test indicator strip comprises a chemical composition which provides a reactive change when subjected to urine of a pregnant woman.

4. A urine test apparatus as set forth in claim 3 wherein said at least one test indicator strip comprises a chemical composition for the detection of human chorionic gonadotropin.

5. A urine test apparatus for use in dilute urine which comprises:
    (a) a biodegradable housing which is substantially planar;
    (b) a tether attached to the biodegradable housing and structured to allow the urine test apparatus to be lowered into and retrieved from a toilet;
    (c) a view site in the planar housing in a predetermined orientation; and
    (d) a test indicator strip affixed within said view site and structured to allow said indicator strip to be viewed from either side of the planar housing, said test indicator strip further comprising a predetermined chemical composition which provides a visible reaction to at least one chemical which may be found in human urine.

6. A urine test apparatus as set forth in claim 5, further comprising a tether attached to the biodegradable housing and structured to allow the urine test apparatus to be lowered into and retrieved from a toilet.

7. A urine test apparatus as set forth in claim 5 wherein said at least one test indicator strip comprises a predetermined chemical composition which provides a reactive change when subjected to urine of a pregnant woman.

8. A urine test apparatus as set forth in claim 7 wherein said at least one test indicator strip comprises a chemical composition for the detection of human chorionic gonadotropin.

9. A urine test apparatus as set forth in claim 2 wherein said at least one test indicator strip is structured to directly contact said fluid absorption device.

10. A urine test apparatus set forth in claim 6 wherein said at least one test indicator strip visibly reacts in the presence of human chorionic gonadotropin.

11. A urine test apparatus as set forth in claim 2 wherein said at least one test indicator strip comprises a monoclonal antibody specific to a predetermined component of human chorionic gonadotropin.

* * * * *

UNITED STATES PATENT AND TRADEMARK OFFICE
CERTIFICATE OF CORRECTION

Patent Number:    6,156,272
Date of Patent:    December 5, 2000
Inventor(s):    Steven H. Lee, Barry F. Lillard It is certified that error appears in the above-identified patent and that said Letters Patent is hereby corrected as shown below:
   ON THE TITLE PAGE Inventor Change:

"Steven H. Lee, Conway Alaska; Barry F. Lillard, Conway Alaska" to

"Steven H. Lee, Conway Arkansas; Barry F. Lillard, Conway Arkansas"

Signed and Sealed this

Eighth Day of May, 2001

*Attest:*

NICHOLAS P. GODICI

*Attesting Officer*     *Acting Director of the United States Patent and Trademark Office*